US011453700B2

(12) United States Patent
Chung et al.

(10) Patent No.: US 11,453,700 B2
(45) Date of Patent: Sep. 27, 2022

(54) PEPTIDE HAVING ACTIVITIES OF SKIN WHITENING AND USES THEREOF

(71) Applicant: CAREGEN CO., LTD., Anyang-si (KR)

(72) Inventors: Yongji Chung, Gunpo-si (KR); Eun Mi Kim, Yongin-si (KR); Eung Ji Lee, Anyang-si (KR)

(73) Assignee: CAREGEN CO., LTD., Anyang-si (KR)

( * ) Notice: Subject to any disclaimer, the term of this patent is extended or adjusted under 35 U.S.C. 154(b) by 0 days.

(21) Appl. No.: 16/625,841

(22) PCT Filed: Oct. 10, 2019

(86) PCT No.: PCT/KR2019/013269
§ 371 (c)(1),
(2) Date: Mar. 11, 2020

(87) PCT Pub. No.: WO2021/033833
PCT Pub. Date: Feb. 25, 2021

(65) Prior Publication Data
US 2022/0169678 A1  Jun. 2, 2022

(30) Foreign Application Priority Data
Aug. 20, 2019 (KR) .......................... 10-2019-0101883

(51) Int. Cl.
| C07K 7/06 | (2006.01) |
| A61K 8/64 | (2006.01) |
| A61Q 19/02 | (2006.01) |
| A61K 38/00 | (2006.01) |

(52) U.S. Cl.
CPC .................. *C07K 7/06* (2013.01); *A61K 8/64* (2013.01); *A61Q 19/02* (2013.01); *A61K 38/00* (2013.01)

(58) Field of Classification Search
CPC .................................. C07K 7/06; A61K 8/64
See application file for complete search history.

(56) References Cited

U.S. PATENT DOCUMENTS

| 8,969,296 B2 | 3/2015 | Chung et al. |
| 10,188,694 B2 | 1/2019 | Cho et al. |
| 2003/0194704 A1 | 10/2003 | Penn et al. |
| 2018/0237475 A1* | 8/2018 | Tagaya .................... A61P 11/06 |
| 2019/0125835 A1 | 5/2019 | Kang et al. |
| 2019/0382445 A1 | 12/2019 | Boo et al. |

FOREIGN PATENT DOCUMENTS

| EP | 2990027 A1 | 3/2016 | |
| KR | 10-2008-0094296 A | 10/2008 | |
| KR | 10-2013-0099480 A | 9/2013 | |
| KR | 10-2017-0113156 A | 10/2017 | |
| KR | 10-2017-0139259 A | 12/2017 | |
| KR | 10-2018-0105106 A | 9/2018 | |
| WO | WO 2008/134659 | * 11/2008 | ............. C07K 16/24 |
| WO | WO-2013/129801 A1 | 9/2013 | |

OTHER PUBLICATIONS

International Search Report dated Jun. 19, 2020 for PCT International Application No. PCT/KR2019/013269, Chung et al., "Peptide Having Activities of Skin Whitening and Uses Thereof," filed Oct. 10, 2019 (5 pages).

Extended European Search Report dated Jan. 28, 2022, for European Application No. 19930169.8, Chung et al., "Peptide having skin whitening activity and use thereof," filed Oct. 10, 2019 (108 pages, including English language versions of documents D5-D9 cited therein, which were cited in an IDS in this case on Aug. 28, 2020).

Pillaiyar et al., "Skin whitening agents: medicinal chemistry perspective of tyrosinase inhibitors," J. Enzyme Inhib. Med. Chem. 32(1):403-425 (2017).

* cited by examiner

*Primary Examiner* — Amber D Steele
(74) *Attorney, Agent, or Firm* — Clark & Elbing LLP; Susan M. Michaud

(57) ABSTRACT

Provided are a peptide having skin-whitening activity and use thereof, and a peptide composed of an amino acid sequence of SEQ ID NO: 1, a skin-whitening cosmetic composition including the peptide, a pharmaceutical composition for preventing or treating a hyperpigmentation disease, the pharmaceutical composition including the peptide, and a method of whitening the skin using the same, or a method of preventing, improving or treating a hyperpigmentation disease using the same.

20 Claims, 7 Drawing Sheets
Specification includes a Sequence Listing.

SEQUENCE LISTING

```
<160> NUMBER OF SEQ ID NOS: 15

<210> SEQ ID NO 1
<211> LENGTH: 5
<212> TYPE: PRT
<213> ORGANISM: Artificial Sequence
<220> FEATURE:
<223> OTHER INFORMATION: Synthetic Construct

<400> SEQUENCE: 1

Pro Asn Arg Tyr Pro
1               5

<210> SEQ ID NO 2
<211> LENGTH: 20
<212> TYPE: DNA
<213> ORGANISM: Artificial Sequence
<220> FEATURE:
<223> OTHER INFORMATION: Synthetic Construct

<400> SEQUENCE: 2
gaaaatagcg ccaagcaccc                                            20

<210> SEQ ID NO 3
<211> LENGTH: 20
<212> TYPE: DNA
<213> ORGANISM: Artificial Sequence
<220> FEATURE:
<223> OTHER INFORMATION: Synthetic Construct

<400> SEQUENCE: 3
cctctttcac tgccctctgg                                            20

<210> SEQ ID NO 4
<211> LENGTH: 20
<212> TYPE: DNA
<213> ORGANISM: Artificial Sequence
<220> FEATURE:
<223> OTHER INFORMATION: Synthetic Construct

<400> SEQUENCE: 4
acgatgtcag gggcaaacat                                            20

<210> SEQ ID NO 5
<211> LENGTH: 20
<212> TYPE: DNA
<213> ORGANISM: Artificial Sequence
<220> FEATURE:
<223> OTHER INFORMATION: Synthetic Construct

<400> SEQUENCE: 5
ctcctctgtg tcagcactgg                                            20

<210> SEQ ID NO 6
<211> LENGTH: 20
<212> TYPE: DNA
<213> ORGANISM: Artificial Sequence
```

```
<220> FEATURE:
<223> OTHER INFORMATION: Synthetic Construct

<400> SEQUENCE: 6
ttctacattg tgggcgccat                                               20

<210> SEQ ID NO 7
<211> LENGTH: 19
<212> TYPE: DNA
<213> ORGANISM: Artificial Sequence
<220> FEATURE:
<223> OTHER INFORMATION: Synthetic Construct

<400> SEQUENCE: 7
tcctccaggt tggtcaatc                                                19

<210> SEQ ID NO 8
<211> LENGTH: 21
<212> TYPE: DNA
<213> ORGANISM: Artificial Sequence
<220> FEATURE:
<223> OTHER INFORMATION: Synthetic Construct

<400> SEQUENCE: 8
ccagcctggc gatcatgtca t                                             21

<210> SEQ ID NO 9
<211> LENGTH: 20
<212> TYPE: DNA
<213> ORGANISM: Artificial Sequence
<220> FEATURE:
<223> OTHER INFORMATION: Synthetic Construct

<400> SEQUENCE: 9
ggtctggaca ggagttgctg                                               20

<210> SEQ ID NO 10
<211> LENGTH: 20
<212> TYPE: DNA
<213> ORGANISM: Artificial Sequence
<220> FEATURE:
<223> OTHER INFORMATION: Synthetic Construct

<400> SEQUENCE: 10
ggccagcttt caggcagagg                                               20

<210> SEQ ID NO 11
<211> LENGTH: 20
<212> TYPE: DNA
<213> ORGANISM: Artificial Sequence
<220> FEATURE:
<223> OTHER INFORMATION: Synthetic Construct

<400> SEQUENCE: 11
tggtgcttca tgggcaaaat                                               20

<210> SEQ ID NO 12
<211> LENGTH: 20
<212> TYPE: DNA
<213> ORGANISM: Artificial Sequence
<220> FEATURE:
<223> OTHER INFORMATION: Synthetic Construct

<400> SEQUENCE: 12
tctgtgaagg tgtgcaggag                                               20
```

```
<210> SEQ ID NO 13
<211> LENGTH: 20
<212> TYPE: DNA
<213> ORGANISM: Artificial Sequence
<220> FEATURE:
<223> OTHER INFORMATION: Synthetic Construct

<400> SEQUENCE: 13
ccgaaacaga gtggaaggtt                                                   20

<210> SEQ ID NO 14
<211> LENGTH: 25
<212> TYPE: DNA
<213> ORGANISM: Artificial Sequence
<220> FEATURE:
<223> OTHER INFORMATION: Synthetic Construct

<400> SEQUENCE: 14
ggtgtgaacg gatttggccg tattg                                             25

<210> SEQ ID NO 15
<211> LENGTH: 25
<212> TYPE: DNA
<213> ORGANISM: Artificial Sequence
<220> FEATURE:
<223> OTHER INFORMATION: Synthetic Construct

<400> SEQUENCE: 15
ccgttgaatt tgccgtgagt ggagt                                             25
```

PEPTIDE HAVING ACTIVITIES OF SKIN WHITENING AND USES THEREOF

SEQUENCE LISTING

The instant application contains a Sequence Listing which has been submitted electronically in ASCII format and is hereby incorporated by reference in its entirety. Said ASCII copy, created on Dec. 20, 2019 is named 51401_016001_Sequence Listing_12.20.19_ST25 and is 3,139 bytes in size.

TECHNICAL FIELD

The present disclosure relates to a peptide having skin-whitening activity and use thereof.

BACKGROUND ART

Factors that determine skin color basically include melasma, freckles, and tanning due to UV exposure, except for differences by race, region, gender, and age, and also include general pigmentation, acne, scars, keratin distribution, blood circulation, stress, health conditions, etc. Among the factors, pigmentation is known as a major factor that determines skin color.

Pigments that affect skin color include melanin, melanoid, carotene, hemoglobin, carotenoid, etc., and various colors of the skin, hair, and eyes are determined by these pigments. Among them, the most important pigment to determine skin color is melanin, and specifically, skin color is determined by the amount and distribution of melanin. Melanin is produced in cells called melanocytes under the skin's epidermis, and is transferred to and pushed away from the stratum corneum by the skin metabolism. Regardless of the skin color, the number of melanocytes is almost the same, but the difference in the skin color is only attributed to the amount, type, and distribution of melanin.

In the skin, tyrosine is converted to DOPA by an enzyme in the human body, called tyrosinase, and a series of oxidation processes finally produce melanin, which is a dark brown polymer. When more melanin is produced than necessary, hyperpigmentation such as melasma, freckles, spots, etc. may be caused, which are cosmetically bad results. Recently, the leisure population has increased and more people enjoy outdoor activities, and thus, there is an increasing demand to prevent melanin pigmentation caused by ultraviolet rays.

Under this technical background, various studies have been conducted on the development of a whitening agent that prevents excessive melanin production through mechanisms such as inhibition of melanocyte activity, inhibition of tyrosinase activity, etc. (Korea Patent Publication No. 10-2019-0050058), but satisfactory results have not yet been obtained.

DESCRIPTION OF EMBODIMENTS

Technical Problem

Provided is a novel peptide having whitening efficacy.
Provided is a cosmetic composition including the peptide.
Provided is a pharmaceutical composition including the peptide.
Provided is a method of preventing, improving, or treating a hyperpigmentation disease using the peptide.

Solution to Problem

An aspect provides a peptide composed of an amino acid sequence of SEQ ID NO: 1.

As used herein, the term "peptide" may refer to a linear molecule formed by binding of amino acid residues to each other by peptide bonds. The peptide may be prepared according to a chemical synthesis method known in the art, in particular, solid-phase synthesis techniques (Merrifield, J. Amer. Chem. Soc. 85:2149-54 (1963); Stewart, et al., Solid Phase Peptide Synthesis, 2nd. ed., Pierce Chem. Co.: Rockford, 111 (1984)) or liquid-phase synthesis techniques (U.S. Pat. No. 5,516,891).

The peptide composed of the amino acid sequence of SEQ ID NO: 1 may have biologically effective activity. The biologically effective activity may exhibit one or more selected from characteristics of (a) inhibition of melanin production; (b) inhibition of tyrosinase activity; and (c) inhibition of expression of Rab27a, melanophilin (Mlph), myosin VA, melanocyte inducing transcription factor (MITF), tyrosinase, or tyrosinase-related protein 1 (TRP1). Therefore, the peptide may be used for whitening the skin or for preventing, improving, or treating a hyperpigmentation disease.

The peptide may be bound with a protecting group at the N-terminus thereof, at the C-terminus thereof, or at both ends thereof to obtain chemical stability, enhanced pharmacological properties (half-life, absorbency, titer, potency, etc.), altered specificity (e.g., broad biological activity spectrum), and reduced antigenicity. The stability may mean not only in vivo stability that protects the peptide from attack of protein cleavage enzymes in vivo, but also storage stability (e.g., room temperature storage stability). The N-terminus of the peptide may be bound with any one protecting group selected from the group consisting of an acetyl group, a fluoreonylmethoxycarbonyl group, a formyl group, a palmitoyl group, a myristyl group, a stearyl group, a butoxycarbonyl group, an allyloxycarbonyl group, and a polyethylene glycol (PEG). The C-terminus of the peptide may be bound with any one protecting group selected from the group consisting of an amino group ($-NH_2$), a tertiary alkyl group, and an azide group ($-NHNH_2$). Further, the peptide may optionally further include a targeting sequence, a tag, a labeled residue, or an amino acid sequence prepared for a specific purpose of increasing half-life or peptide stability.

Another aspect provides a cosmetic composition including the peptide including the amino acid sequence of SEQ ID NO: 1 as an active ingredient; a pharmaceutical composition including the peptide including the amino acid sequence of SEQ ID NO: 1 as an active ingredient; and use of the peptide including the amino acid sequence of SEQ ID NO: 1 for the preparation of the cosmetic or pharmaceutical composition, or for being used as the cosmetic or pharmaceutical composition.

Still another aspect provides a skin-whitening cosmetic composition including the peptide composed of the amino acid sequence of SEQ ID NO: 1 as an active ingredient.

The peptide is the same as described above.

The term "skin whitening" means not only brightening skin tone by inhibiting the synthesis of melanin pigments, but also improving skin hyperpigmentation caused by ultraviolet light, hormones, or heredity. Hyperpigmentation of the skin may include melasma, freckles, lentigo, blemish, lentigo senilis, or brown spots, etc.

Existing functional peptides, despite their effective biological activity, have disadvantages that they do not effectively enter target tissues or cells due to their own size or are cleared in the body in a short time due to the short half-life. In contrast, the skin-whitening cosmetic composition according to one embodiment includes the peptide consisting of 10 amino acids or less as an active ingredient, and therefore, the active ingredient has a very excellent skin penetration rate. For example, when topically applied to the skin, the composition may exhibit an effective skin whitening effect.

The term "improving" may mean all actions that at least reduce a parameter related to the condition being alleviated or treated, for example, the degree of a symptom.

The cosmetic composition may include a cosmetically effective amount of the peptide; and/or a cosmetically acceptable carrier. The term "cosmetically effective amount" means an amount sufficient to achieve the skin-whitening efficacy of the cosmetic composition. The cosmetically effective amount may be determined by those skilled in the art, based on a common knowledge, such that the skin whitening effect is exhibited. A weight ratio of the peptide and the cosmetically acceptable carrier may be, for example, 500:1 to 1:500, and for example, the weight ratio may be 450:1 to 1:450, 400:1 to 1:400, 350:1 to 1:350, 300:1 to 1:300, 250:1 to 1:250, 200:1 to 1:200, 150:1 to 1:150, 100:1 to 1:100, 80:1 to 1:80, 60:1 to 1:60, 40:1 to 1:40, 20:1 to 1:20, 10:1 to 1:10, 8:1 to 1:8, 6:1 to 1:6, 4:1 to 1:4, or 2:1 to 1:2, but is not limited thereto.

The cosmetic composition may be prepared in any formulation commonly prepared in the art, and for example, may be formulated into a solution, a suspension, an emulsion, a paste, a gel, a cream, a lotion, a powder, a soap, a surfactant-containing cleanser, oil, a powder foundation, an emulsion foundation, a wax foundation, a spray, etc., but is not limited thereto. For example, the cosmetic composition may be prepared in the formulation of a softening lotion, a nutrition lotion, a nutrition cream, a massage cream, an essence, an eye cream, a cleansing cream, a cleansing foam, cleansing water, a pack, a spray, a powder, etc.

When the formulation of the cosmetic composition is a paste, cream, or gel, animal oil, vegetable oil, wax, paraffin, starch, tragacanth, a cellulose derivative, polyethylene glycol, silicone, bentonite, silica, talc, zinc oxide, etc. may be used as a carrier component.

When the formulation of the cosmetic composition is a powder or a spray, lactose, talc, silica, aluminum hydroxide, calcium silicate or polyamide powder may be used as a carrier component. For example, in the case of a spray, a propellant such as chlorofluorohydrocarbon, propane/butane, or dimethyl ether may be additionally included.

When the formulation of the cosmetic composition is a solution or an emulsion, a solvent, a solubilizing agent, or an emulsifying agent may be used as a carrier component. For example, water, ethanol, isopropanol, ethyl carbonate, ethyl acetate, benzyl alcohol, benzyl benzoate, propylene glycol, 1,3-butylglycol oil, glycerol aliphatic ester, polyethyleneglycol, or fatty acid ester of sorbitan may be included.

When the formulation of the cosmetic composition is a suspension, a liquid diluent such as water, ethanol, or propylene glycol, a suspending agent such as ethoxylated isostearyl alcohol, polyoxyethylene sorbitol ester, and polyoxyethylene sorbitan ester, microcrystalline cellulose, aluminum metahydroxide, bentonite, agar, tragacanth, etc. may be used as a carrier component.

When the formulation of the cosmetic composition is a surfactant-containing cleanser, aliphatic alcohol sulfate, aliphatic alcohol ether sulfate, sulfosuccinic acid monoester, isethionate, an imidazolium derivative, methyltaurate, sarcosinate, fatty acid amide ether sulfate, alkylamidobetaine, aliphatic alcohol, fatty acid glyceride, fatty acid diethanolamide, vegetable oil, a lanolin derivative, ethoxylated glycerol fatty acid ester, etc. may be used as a carrier component.

In addition to the peptide as an active ingredient and the carrier component, the cosmetic composition may include ingredients commonly used in cosmetic compositions, for example, a common auxiliary agent such as an antioxidant, a stabilizer, a solubilizer, vitamins, a pigment, and a flavoring agent.

Still another aspect provides a pharmaceutical composition for preventing or treating a hyperpigmentation disease, the pharmaceutical composition including the peptide composed of the amino acid sequence of SEQ ID NO: 1 as an active ingredient.

The peptide is the same as described above.

The term "preventing" refers to all actions that inhibit or slow down the onset of a disease by the administration of the composition. The term "treating" refers to any form of treatment that provides an individual suffering from or at risk of developing a disease with effects including improving conditions (e.g., one or more symptoms) of the individual, delaying disease progression, delaying the onset of symptoms, slowing of symptom progression, etc. Thus, the "treating" and "preventing" do not mean the curing or complete elimination of symptoms.

The "hyperpigmentation disease" refers to a disease in which melanin pigment is excessively produced and deposited on the skin, i.e., hyperpigmentation symptoms. The hyperpigmentation disease may be, for example, melasma, freckles, lentigo, blemish, lentigo senilis, or solar lentigines.

The pharmaceutical composition may include a pharmaceutically effective amount of the peptide; and/or a pharmaceutically acceptable carrier.

The term "pharmaceutically effective amount" may mean an amount sufficient to achieve the efficacy of the pharmaceutical composition to prevent or treat a hyperpigmentation disease.

A weight ratio of the peptide and the pharmaceutically acceptable carrier may be, for example, 500:1 to 1:500. For example, the weight ratio may be 450:1 to 1:450, 400:1 to 1:400, 350:1 to 1:350, 300:1 to 1:300, 250:1 to 1:250, 200:1 to 1:200, 150:1 to 1:150, 100:1 to 1:100, 80:1 to 1:80, 60:1 to 1:60, 40:1 to 1:40, 20:1 to 1:20, 10:1 to 1:10, 8:1 to 1:8, 6:1 to 1:6, 4:1 to 1:4, or 2:1 to 1:2, but is not limited thereto.

The pharmaceutically acceptable carrier is those commonly used in the preparation, and may include lactose, dextrose, sucrose, sorbitol, mannitol, starch, acacia rubber, calcium phosphate, alginate, gelatin, calcium silicate, microcrystalline cellulose, polyvinylpyrrolidone, cellulose, water, syrup, methyl cellulose, methylhydroxybenzoate, propylhydroxybenzoate, talc, magnesium stearate, mineral oil, etc., but is not limited thereto. Appropriate pharmaceutically acceptable carriers and formulations are described in detail in Remington's Pharmaceutical Sciences (19th ed., 1995).

The pharmaceutical composition may further include a lubricant, a wetting agent, a sweetener, a flavoring agent, an emulsifier, a suspending agent, a preservative, etc., in addition to the above components, but is not limited thereto.

The pharmaceutical composition may be administered orally or parenterally, and specifically parenterally. The parenteral administration may include intramuscular injection, intravenous injection, subcutaneous injection, intraperitoneal injection, topical administration, transdermal administration, etc., but is not limited thereto.

An administration dose of the pharmaceutical composition may be 0.0001 μg to 1000 μg (microgram), 0.001 μg to 1000 μg, 0.01 μg to 1000 μg, 0.1 μg to 1000 μg, or 1.0 μg to 1000 µg per day, but is not limited thereto. The administration may be performed once a day to four times a day, twice a day to three times a day, or twice a day. Further, the administration of the present disclosure may be performed for 4 weeks or more, 8 weeks or more, 4 weeks to 12 weeks, or 8 weeks to 12 weeks. The administration may be prescribed in various ways depending on factors such as a formulation method, administration mode, a patient's age, weight, sex, disease conditions, food, administration time, administration route, excretion rate, and response sensitivity.

The pharmaceutical composition may be prepared in a unit dose form or may be prepared into a multidose container by formulating the pharmaceutical composition using a pharmaceutically acceptable carrier and/or excipient according to a method, which may be easily carried out by those skilled in the art to which the present disclosure pertains.

The formulation may be a solution, suspension, or emulsion form in an oil or aqueous medium, or may be an extract, powder, granule, tablet, or capsule form, and may further include a dispersing agent and/or a stabilizer.

Still another aspect provides a method of whitening the skin, the method including applying, to the skin of an individual, the cosmetic composition including the peptide composed of the amino acid sequence of SEQ ID NO: 1 as an active ingredient.

The peptide, skin whitening, and cosmetic composition are the same as described above.

The terms "spreading", "applying", and "administering" may be used interchangeably, and may mean at least partial localization of the composition according to one embodiment to a desired site, or placement of the composition according to one embodiment into an individual via a route of administration.

Still another aspect provides a method of preventing, improving, or treating a hyperpigmentation disease, the method including administering, to an individual, the pharmaceutical composition including the peptide composed of the amino acid sequence of SEQ ID NO: 1.

The peptide, pharmaceutical composition, hyperpigmentation disease, preventing, improving, and treating are the same as described above.

The term "individual" means a subject in need of treatment of a disease, and more specifically, a mammal, such as a human or non-human primate, a mouse, a dog, a cat, a horse, and a cow.

Still another aspect provides a skin-whitening food composition including the peptide composed of the amino acid sequence of SEQ ID NO: 1 as an active ingredient.

The peptide and skin whitening are the same as described above.

Content of the peptide as an active ingredient in the food composition may be appropriately selected without limitation depending on the form of the food, use thereof, etc. For example, the peptide may be added in an amount of 0.01% by weight to 15% by weight, based on the total weight of the food. For example, the peptide may be added in a proportion of 0.02 g to 10 g, or 0.3 g to 1 g, based on 100 mL of a health drink composition.

Advantageous Effects of Disclosure

A peptide according to an aspect significantly inhibits melanin production and tyrosinase activity as well as expression of factors associated with melanin production, thereby exhibiting excellent skin-whitening effect and being applied in preventing, improving, or treating a hyperpigmentation disease. Accordingly, the peptide according to an aspect may be applied as an active ingredient for a skin-whitening composition or a pharmaceutical composition for treating or preventing a hyperpigmentation disease.

MODE OF DISCLOSURE

Hereinafter, the present disclosure will be described in more detail with reference to embodiments. However, these embodiments are for illustrative purposes only, and the scope of the present disclosure is limited to these embodiments.

Example 1. Synthesis of Peptide

A peptide having an amino acid sequence of SEQ ID NO: 1 described in the following [Table 1] was synthesized using an automated peptide synthesizer (Milligen 9050, Millipore, USA), and pure peptide was isolated using a C18 reversed phase high performance liquid chromatography (HPLC) (Waters Associates, USA). ACQUITY UPLC BEH300 C18 (2.1 mm×100 mm, 1.7 µm, Waters Co, USA) was used as a column.

TABLE 1

| SEQ ID NO: | Peptide sequence |
|---|---|
| 1 | PNRYP |

Example 2. Whitening Efficacy of Synthesized Peptide (1) Examination of Inhibitory Effect on Melanin Production A mouse melanoma cell B16F10 was seeded in a 6-well plate at a density of 5×10⁴ cells/well, followed by incubation for 16 hours. Thereafter, the culture medium was replaced by a medium supplemented with 2% (v/v) serum, and then 200 ng/mL of α-melanocyte-stimulating hormones (α-MSH) was added thereto to stimulate melanin production, together with each peptide of an amino acid sequence of SEQ ID NO: 1, at a concentration of 10 µM, 50 µM, 100 µM, or 200 µM, respectively, followed by incubation for 72 hours. Thereafter, the incubated cells were dissolved in 1 N NaOH, and absorbance at 450 nm was measured. In addition, an untreated group (Con) was used as a control, and only an α-MSH-treated group as a negative control and 200 µM or 500 µM of arbutin-, which is a known skin-whitening agent, and α-MSH-treated group as a positive control were used.

Figure 1:
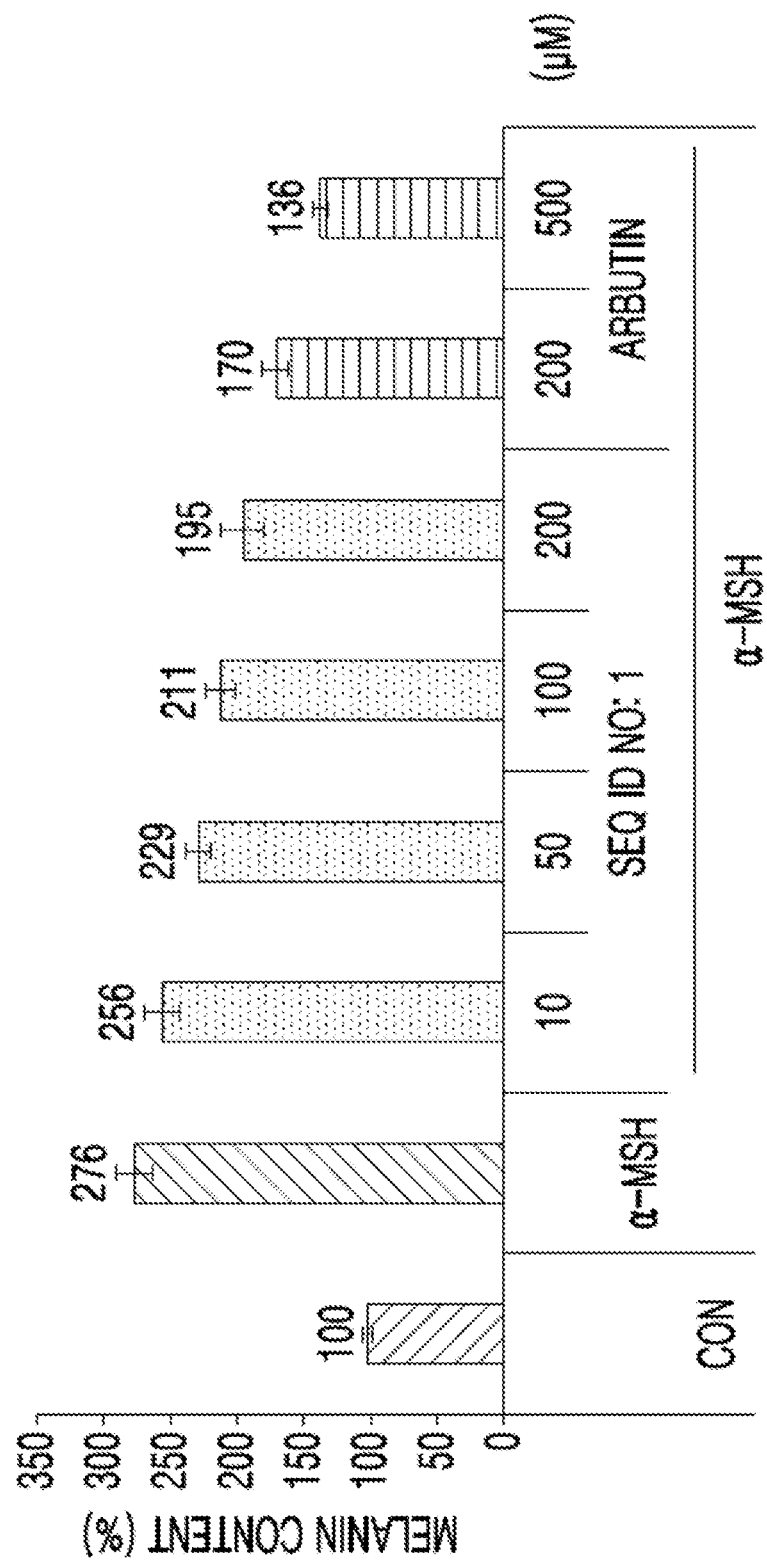
FIG. 1 shows results of examining reduction of melanin production, after adding a peptide having an amino acid sequence of SEQ ID NO: 1 to B16F10 cells.

From absorbance at 450 nm, the content of melanin (%) produced by B16F10 cells was determined. The determined content of melanin (%) is shown in FIG. 1. As shown in FIG. 1, it was confirmed that melanin production was reduced in a concentration-dependent manner by addition of the peptide composed of the amino acid sequence of SEQ ID NO: 1.

(2) Examination of Inhibitory Effect on Tyrosinase Activity

Inhibitory effect of the peptide of SEQ ID NO: 1 on tyrosinase activity, which is a key enzyme in melanin production, was examined.

In detail, a mouse melanoma cell B16F10 was seeded in a 6-well plate at a density of $5×10^4$ cells/well, followed by incubation for 16 hours. Thereafter, the culture medium was replaced by a medium supplemented with 2% (v/v) serum, and then 200 ng/mL of α-MSH was added thereto. Together therewith, the peptide composed of the amino acid sequence of SEQ ID NO: 1 was added at a concentration of 1 μM, 10 μM, 20 μM, 40 μM, 60 μM, 80 μM or 160 μM, respectively, followed by incubation for 72 hours. The 6-well plate was placed on ice, and then washed with cold PBS twice. Thereafter, the cells were lysed by adding 0.1 M sodium phosphate buffer (pH 6.8, lysis buffer) containing 1% (v/v) triton X-100. Thereafter, the cells in the well plate were scraped using a scraper, and collected in a 1.5 mL tube. The collected cells were vortexed, and centrifuged at 15,000 rpm for 10 minutes to obtain a supernatant. Thereafter, proteins in the supernatant were quantified to adjust the protein content at a predetermined amount. A buffer was added thereto, and 90 μL total of the sample was dispensed in a 96-well plate. Further, an experimental sample, a blank sample, and a positive control sample were prepared in the plate as shown in Table 2 below.

TABLE 2

|  | Experimental sample | Blank sample | Positive control sample |
|---|---|---|---|
| Sample | 90 μL | — | — |
| Buffer | — | 90 μL | 90 μL |
| Mushroom tyrosinase (0.1 mg/mL) | — | — | 10 μL |

Figure 2:
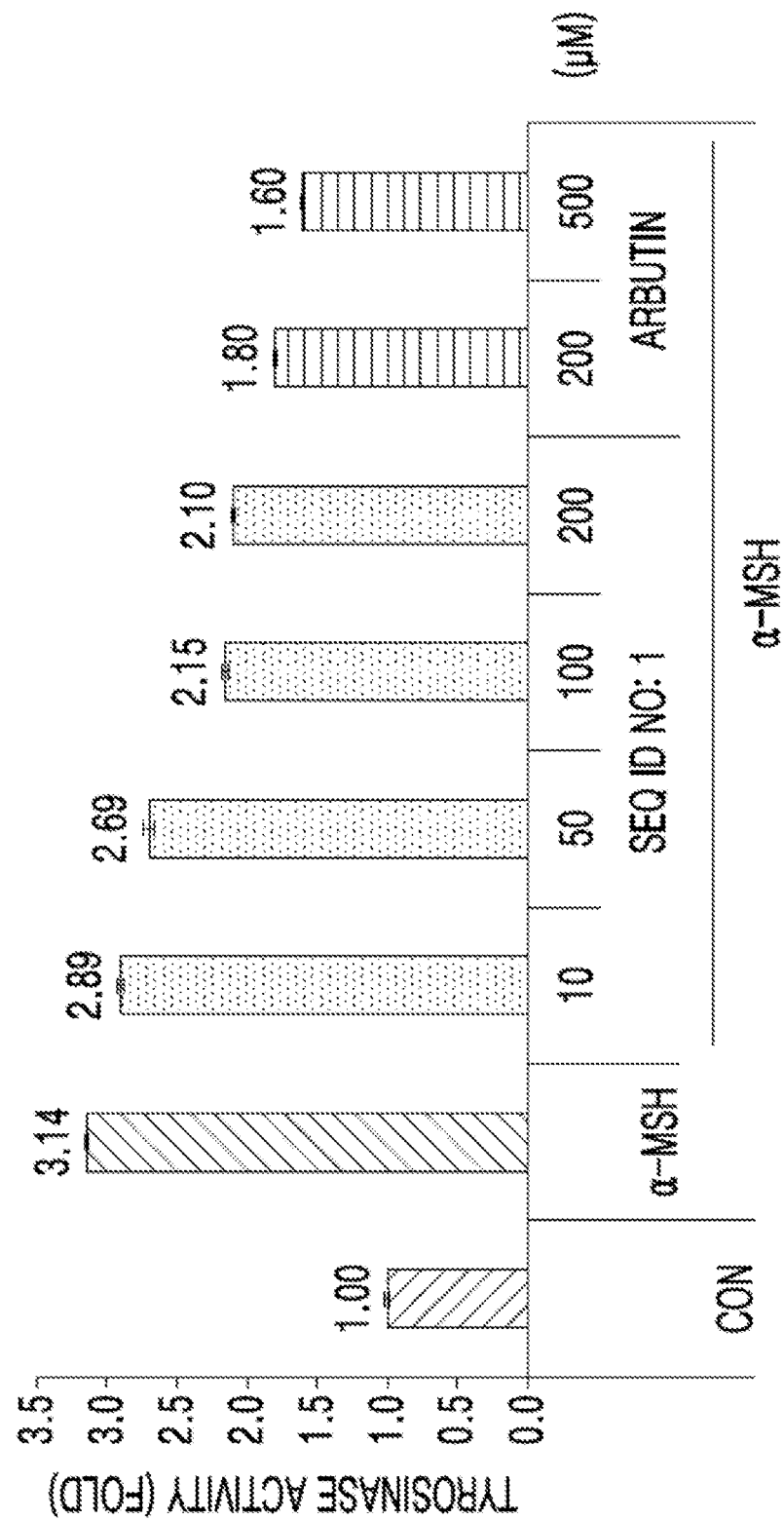
FIG. 2 shows results of examining reduction of tyrosinase activity, after adding the peptide to B16F10 cells.

Thereafter, 20 μL of 10 mM L-DOPA was added to each sample, and incubated at 37° C. for 1 hour. Then, absorbance at 475 nm was measured. Moreover, an untreated group (Con) was used as a control, and only α-MSH-treated group as a negative control and 200 μM or 500 μM of arbutin-, which is a known skin-whitening agent, and α-MSH-treated group as a positive control were used. From absorbance at 450 nm, the tyrosinase activity (fold) was determined. The determined tyrosinase activity (fold) is shown in FIG. 2. As shown in FIG. 2, it was confirmed that tyrosinase activity was inhibited by addition of the peptide composed of the amino acid sequence of SEQ ID NO: 1.

(3) Examination of Inhibitory Effect on Expression of Melanin Production-associated Genes Inhibitory effect of the peptide of SEQ ID NO: 1 on melanin production-associated genes was examined.

In detail, a mouse melanoma cell B16F10 was seeded in a 6-well plate at a density of $5×10^4$ cells/well, followed by incubation for 16 hours. Thereafter, the culture medium was replaced by a medium supplemented with 2% (v/v) serum, and then 200 ng/mL of α-MSH was added thereto. Together therewith, the peptide composed of the amino acid sequence of SEQ ID NO: 1 was added at a concentration of 1 μM, 10 μM, 20 μM, 40 μM, 60 μM, 80 μM or 160 μM, respectively, followed by incubation for 72 hours. mRNAs were extracted from the cultured cells, and the extracted mRNAs were reverse transcribed using a cDNA synthesis kit & PCR pre-mix (Intron, Korea), thereby synthesizing cDNA, respectively. Thereafter, a polymerase chain reaction (PCR) was carried out using each cDNA and Rab27a, Melanophilin (Mlph), myosin VA, MITF, tyrosinase, or TRP1 primer pairs. Moreover, a control, a negative control, and a positive control were used in the same manner as in Example 2.(1), and nucleotide sequences of the primers used herein are as in Table 3 below.

TABLE 3

| Primer | | Nucleotide sequence (5'->3') | SEQ ID NO: |
|---|---|---|---|
| Rab27a | Forward | GAAAATAGCGCCAAGCACCC | 2 |
|  | Reverse | CCTCTTTCACTGCCCTCTGG | 3 |
| Mlph | Forward | ACGATGTCAGGGGCAAACAT | 4 |
|  | Reverse | CTCCTCTGTGTCAGCACTGG | 5 |
| Myosin VA | Forward | TTCTACATTGTGGGCGCCAT | 6 |
|  | Reverse | TCCTCCAGGTTGGTCAATC | 7 |
| MITF | Forward | CCAGCCTGGCGATCATGTCAT | 8 |
|  | Reverse | GGTCTGGACAGGAGTTGCTG | 9 |
| Tyrosinase | Forward | GGCCAGCTTTCAGGCAGAGG | 10 |
|  | Reverse | TGGTGCTTCATGGGCAAAAT | 11 |
| TRP1 | Forward | TCTGTGAAGGTGTGCAGGAG | 12 |
|  | Reverse | CCGAAACAGAGTGGAAGGTT | 13 |
| GAPDH | Forward | GGTGTGAACGGATTTGGCCGTATTG | 14 |
|  | Reverse | CCGTTGAATTTGCCGTGAGTGGAGT | 15 |

Figure 3:
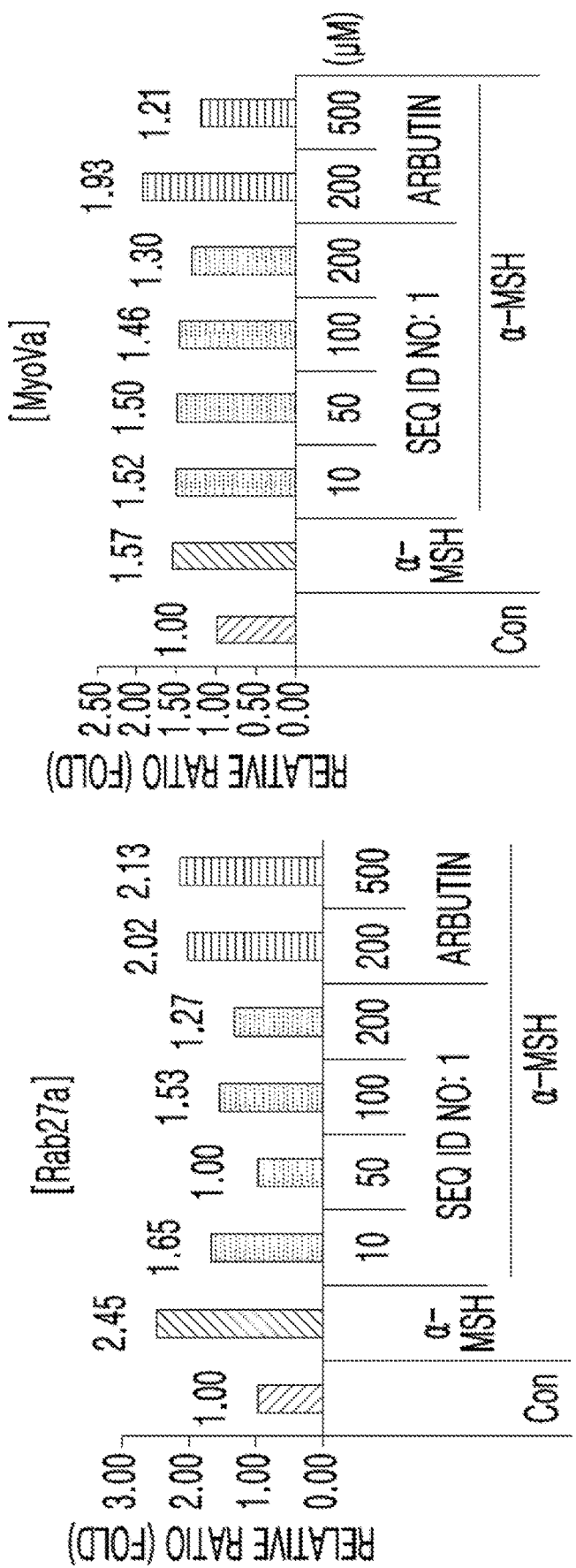
FIG. 3 shows results of examining inhibition of expression of Rab27a, Mlph, myosin VA, MITF, tyrosinase, and TRP1, which are genes associated with melanin production, after adding the peptide to B16F10 cells.
Figure 3:
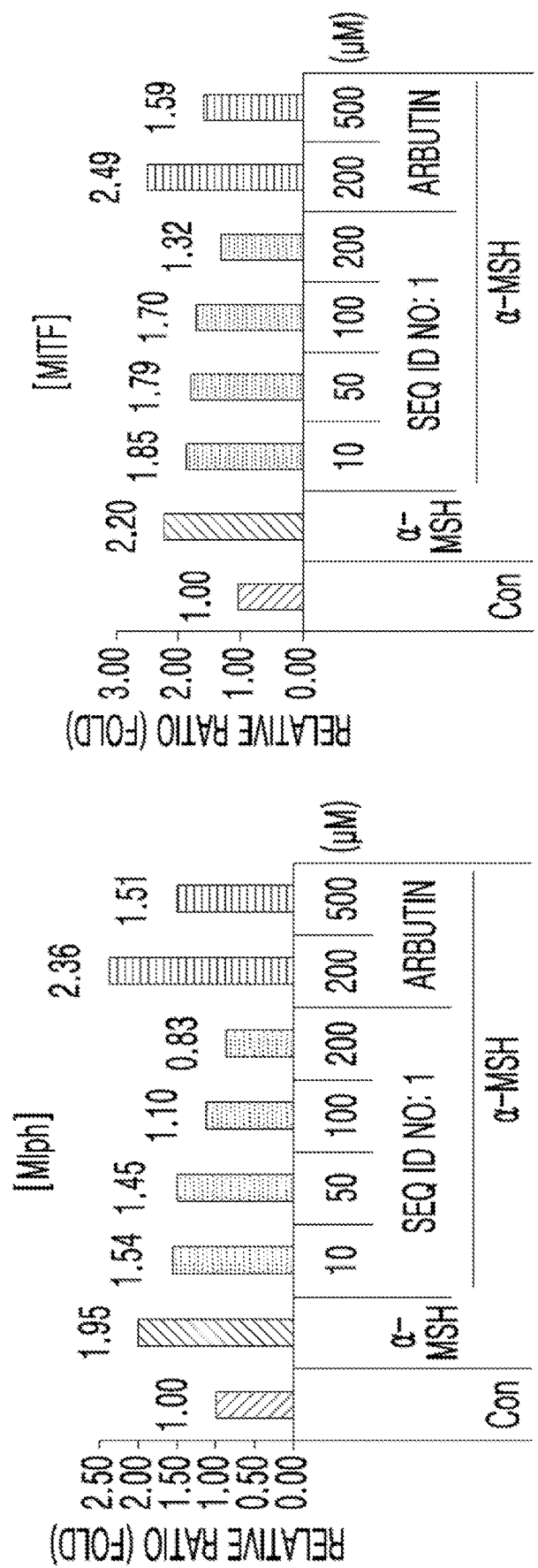
Figure 3:
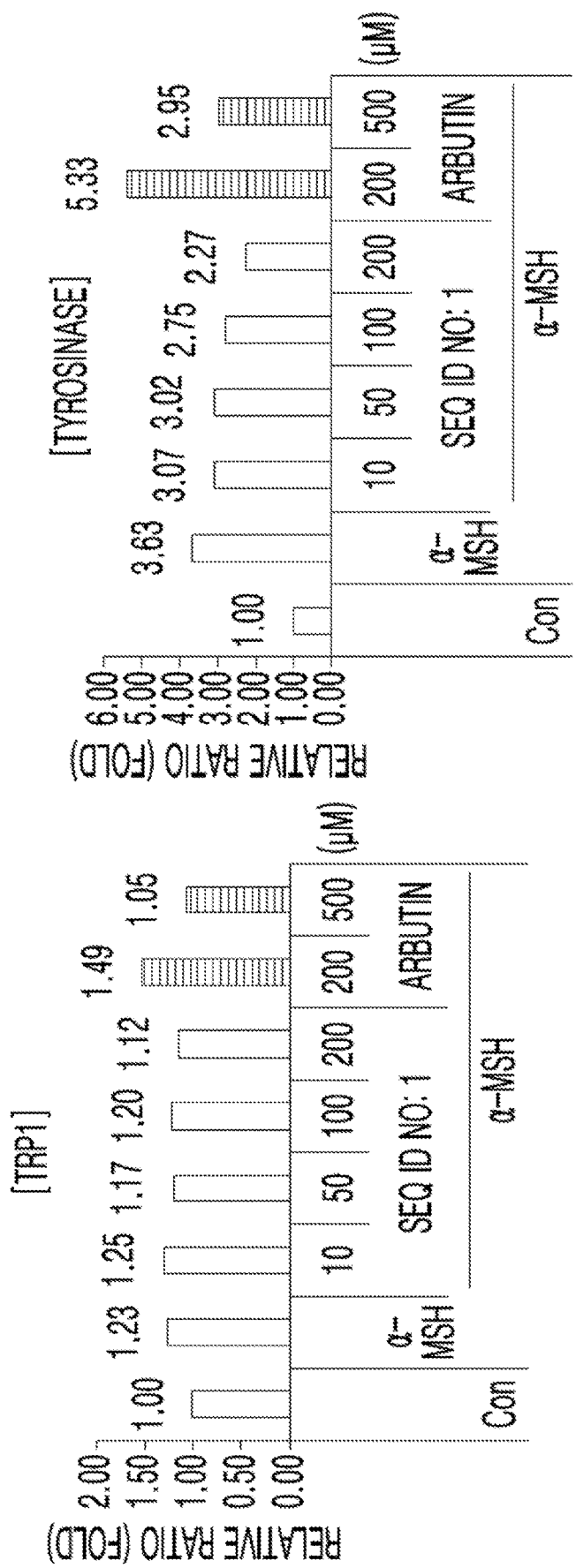

Changes in the expression determined from the PCR amplification results are shown in FIG. 3. As shown in FIG. 3, it was confirmed that expression of Rab27a, Mlph, myosin VA, MITF, tyrosinase, and TRP1, which are melanin production-associated genes, was inhibited by addition of the peptide composed of the amino acid sequence of SEQ ID NO: 1.

(4) Examination of Inhibitory Effect on Expression of Melanin Production-associated Proteins Inhibitory effect of the peptide of SEQ ID NO: 1 on melanin production-associated proteins was examined.

In detail, a mouse melanoma cell B16F10 was seeded in a 6-well plate at a density of $5×10^4$ cells/well, followed by incubation for 16 hours. Thereafter, the culture medium was replaced by a medium supplemented with 2% (v/v) serum, and then 200 ng/mL of α-MSH was added thereto. Together therewith, the peptide composed of the amino acid sequence of SEQ ID NO: 1 was added at a concentration of 1 μM, 10 μM, 20 μM, 40 μM, 60 μM, 80 μM or 160 μM, respectively, followed by incubation for 72 hours. Thereafter, the cultured cells were lysed, and then subjected to immunoblotting using antibodies (all available from santacruz biotechnology, USA) against Mlph, Rab27a, tyrosinase (TYR), or MITF. In addition, a control, a negative control, and a positive control were used in the same manner as in Example 2.(1).

Figure 4:
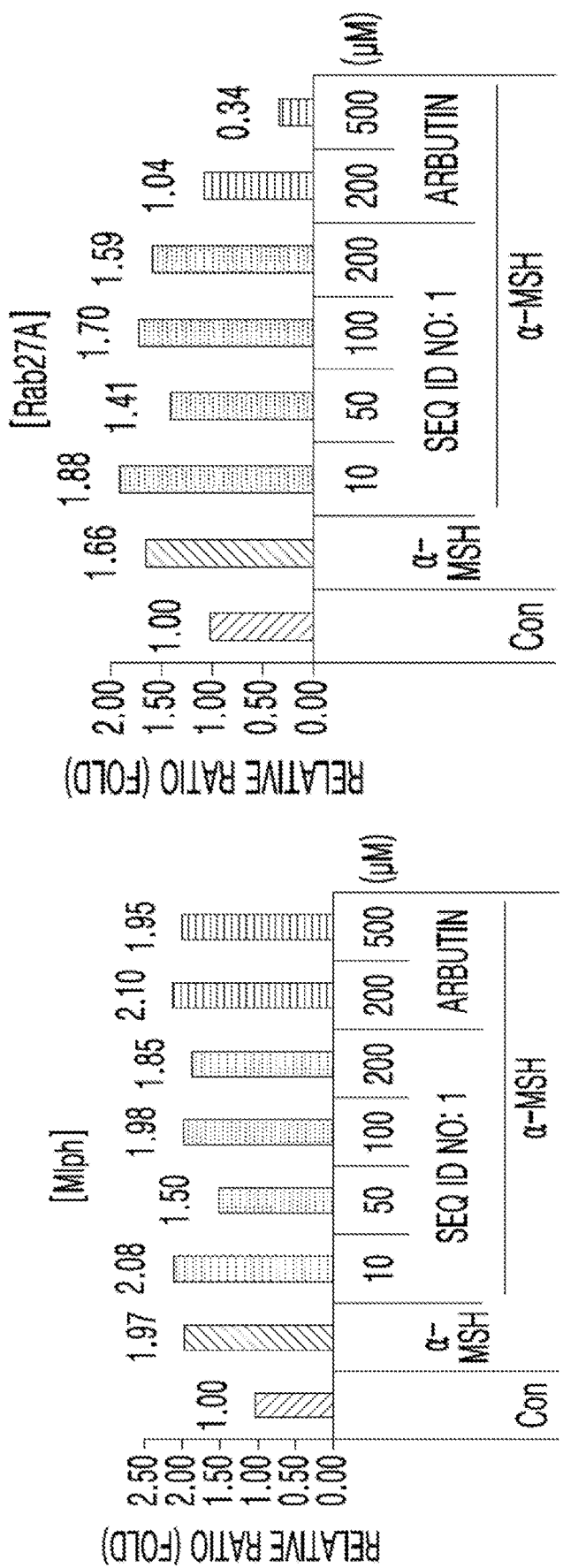
FIG. 4 shows results of examining inhibition of expression of Mlph, Rab27a, tyrosinase (TYR), and MITF, which are proteins associated with melanin production, after adding the peptide to B16F10 cells.
Figure 4:
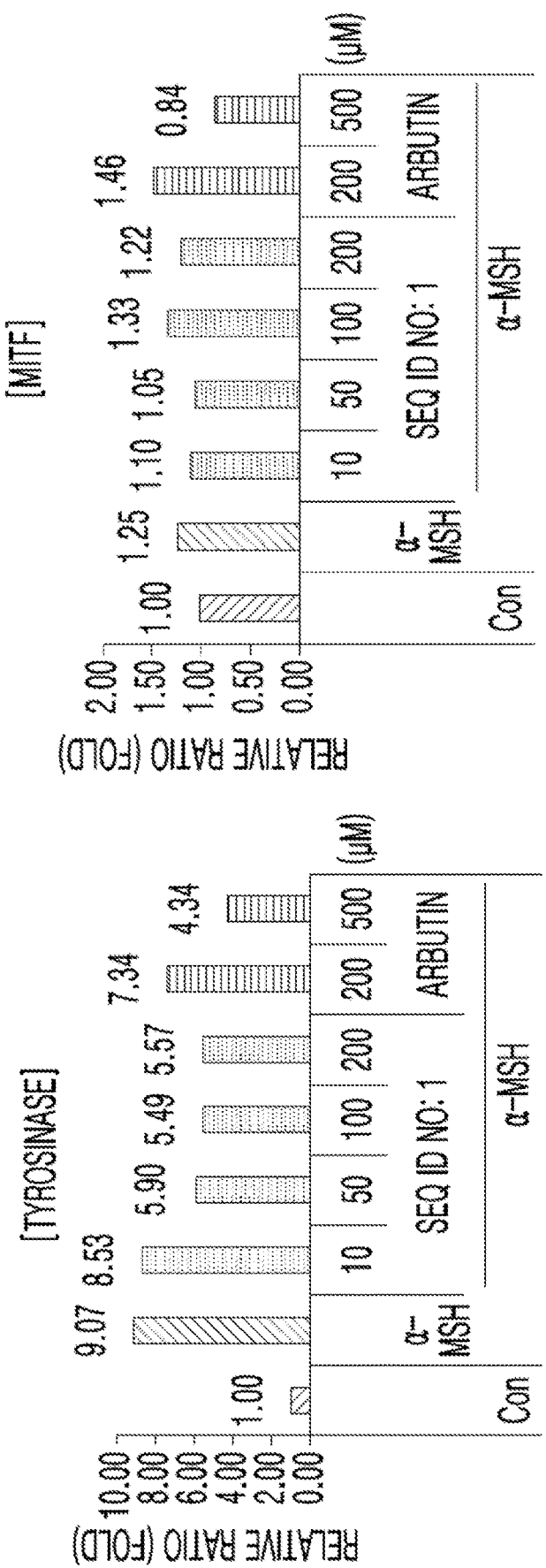

Changes in the expression determined from the immunoblotting results are shown in FIG. 4. As shown in FIG. 4, it was confirmed that expression of Mlph, Rab27, TYR, and MITF, which are melanin production-associated proteins, was inhibited by addition of the peptide composed of the amino acid sequence of SEQ ID NO: 1.

Taken together, the above experimental results indicate that the peptide composed of the amino acid sequence of SEQ ID NO: 1 according to one embodiment has skin-whitening efficacy.

The invention claimed is:

1. A peptide consisting of the amino acid sequence of SEQ ID NO: 1, optionally wherein: (i) the N-terminus of the peptide is bound with any one protecting group selected from the group consisting of an acetyl group, a fluoreonyl-methoxycarbonyl group, a formyl group, a palmitoyl group, a myristyl group, a stearyl group, and a polyethylene glycol (PEG), and/or (ii) the C-terminus of the peptide is bound with any one protecting group selected from the group consisting of an amino group (—NH$_2$) and an azide group (—NHNH$_2$).

2. A skin-whitening cosmetic composition comprising the peptide of claim 1 as an active ingredient.

3. A pharmaceutical composition for preventing or treating a hyperpigmentation disease, the pharmaceutical composition comprising the peptide of claim 1 as an active ingredient.

4. The pharmaceutical composition of claim 3, wherein the hyperpigmentation disease is melasma, freckles, lentigo, blemish, lentigo senilis, or solar lentigines.

5. The peptide of claim 1, wherein the N-terminus of the peptide is bound with any one protecting group selected from the group consisting of an acetyl group, a fluoreonyl-methoxycarbonyl group, a formyl group, a palmitoyl group, a myristyl group, a stearyl group, and a polyethylene glycol (PEG).

6. A skin-whitening cosmetic composition comprising the peptide of claim 5 as an active ingredient.

7. A pharmaceutical composition for preventing or treating a hyperpigmentation disease, the pharmaceutical composition comprising the peptide of claim 5 as an active ingredient.

8. The pharmaceutical composition of claim 7, wherein the hyperpigmentation disease is melasma, freckles, lentigo, blemish, lentigo senilis, or solar lentigines.

9. The peptide of claim 1, wherein the C-terminus of the peptide is bound with any one protecting group selected from the group consisting of an amino group (—NH$_2$) and an azide group (—NHNH$_2$).

10. A skin-whitening cosmetic composition comprising the peptide of claim 9 as an active ingredient.

11. A pharmaceutical composition for preventing or treating a hyperpigmentation disease, the pharmaceutical composition comprising the peptide of claim 9 as an active ingredient.

12. The pharmaceutical composition of claim 11, wherein the hyperpigmentation disease is melasma, freckles, lentigo, blemish, lentigo senilis, or solar lentigines.

13. The peptide of claim 1, wherein the peptide exhibits any one or more selected from the following characteristics:
   (a) inhibition of melanin production;
   (b) inhibition of tyrosinase activity; and
   (c) inhibition of expression of Rab27a, melanophilin (Mlph), myosin VA, melanocyte inducing transcription factor (MITF), tyrosinase, or tyrosinase-related protein 1 (TRP1).

14. A skin-whitening cosmetic composition comprising the peptide of claim 13 as an active ingredient.

15. A pharmaceutical composition for preventing or treating a hyperpigmentation disease, the pharmaceutical composition comprising the peptide of claim 13 as an active ingredient.

16. The pharmaceutical composition of claim 15, wherein the hyperpigmentation disease is melasma, freckles, lentigo, blemish, lentigo senilis, or solar lentigines.

17. A method of whitening the skin, the method comprising applying, to the skin of an individual, a cosmetic composition comprising the peptide of claim 1 as an active ingredient.

18. A method of whitening the skin, the method comprising applying, to the skin of an individual, a cosmetic composition comprising the peptide of claim 5 as an active ingredient.

19. A method of whitening the skin, the method comprising applying, to the skin of an individual, a cosmetic composition comprising the peptide of claim 9 as an active ingredient.

20. A method of whitening the skin, the method comprising applying, to the skin of an individual, a cosmetic composition comprising the peptide of claim 13 as an active ingredient.

\* \* \* \* \*